(12) United States Patent
Goto et al.

(10) Patent No.: US 8,971,607 B2
(45) Date of Patent: Mar. 3, 2015

(54) X-RAY CT APPARATUS AND IMAGE RECONSTRUCTION METHOD

(75) Inventors: Taiga Goto, Tokyo (JP); Hisashi Takahashi, Tokyo (JP); Koichi Hirokawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 134 days.

(21) Appl. No.: 13/989,564

(22) PCT Filed: Dec. 7, 2011

(86) PCT No.: PCT/JP2011/078234
§ 371 (c)(1),
(2), (4) Date: May 24, 2013

(87) PCT Pub. No.: WO2012/077694
PCT Pub. Date: Jun. 14, 2012

(65) Prior Publication Data
US 2013/0243299 A1    Sep. 19, 2013

(30) Foreign Application Priority Data

Dec. 10, 2010   (JP) ................................. 2010-275278

(51) Int. Cl.
| | |
|---|---|
| G06K 9/00 | (2006.01) |
| G06T 11/00 | (2006.01) |
| A61B 6/03 | (2006.01) |
| A61B 6/00 | (2006.01) |

(52) U.S. Cl.
CPC ............. *G06T 11/003* (2013.01); *G06T 11/006* (2013.01); *A61B 6/032* (2013.01); *A61B 6/4078* (2013.01); *G06T 2211/421* (2013.01)
USPC .......................................................... 382/131

(58) Field of Classification Search
None
See application file for complete search history.

(56) References Cited

U.S. PATENT DOCUMENTS

| | | | | |
|---|---|---|---|---|
| 6,028,908 A | * | 2/2000 | Taguchi | .......................... 378/15 |
| 2005/0175143 A1 | * | 8/2005 | Miyazaki et al. | ............... 378/19 |

FOREIGN PATENT DOCUMENTS

| | | | | |
|---|---|---|---|---|
| JP | 1-181847 | | 7/1989 | |
| JP | 6-181919 | | 7/1994 | |
| JP | 10-286253 | | 10/1998 | |
| JP | 10-314161 | | 12/1998 | |
| JP | 2005-224637 | | 8/2005 | |
| JP | 2009-089810 | * | 10/2007 | ............... A61B 6/03 |
| JP | 2009-089810 | | 4/2009 | |

OTHER PUBLICATIONS

International Search Report in PCT/JP2011/078234.

* cited by examiner

*Primary Examiner* — Amara Abdi
(74) *Attorney, Agent, or Firm* — Cooper & Dunham LLP

(57) ABSTRACT

In order to execute a high-resolution reconstructible distance-driven back projection process and to generate a high-resolution tomographic image, an X-ray CT apparatus 1 determines the presence/absence of opposing data corresponding to each piece of target data on the basis of scanning conditions, and calculates a phase range where opposing data is present (Step 21). The X-ray CT apparatus 1 performs high-resolution conversion of a zero-insertion method on a phase range where opposing data is present, and performs high-resolution conversion using a data interpolation method on a phase range where no opposing data is present, thereby creating double sampled high-resolution projection data, and calculates a view weight (Step 22). The X-ray CT apparatus 1 performs a distance-driven high-resolution back projection process using high-resolution projection data and generates a reconstructed image (Step 23).

8 Claims, 16 Drawing Sheets

X-RAY CT APPARATUS AND IMAGE RECONSTRUCTION METHOD

TECHNICAL FIELD

The present invention relates to an X-ray CT apparatus or the like which irradiates an X-ray onto an object, measures an X-ray transmitted through the object by an X-ray detector, and reconstructs projection data from multiple directions to obtain a tomographic image of the object, and in particular, to an image reconstruction process.

BACKGROUND ART

As an image reconstruction method which generates tomographic image data from projection data obtained by scanning of an X-ray CT apparatus, a Fourier transform method, a filtered back projection method, an iterative approximation method, and the like have been suggested.

In general, from the viewpoint of the calculation time, calculation precision, and the memory usage, a filtered back projection method is used. Meanwhile, in the iterative approximation method, although a sequential projection process and a back projection process are performed iteratively, the calculation time and the memory usage become problematic, there are features of noise reduction, artifact reduction, and the like. Accordingly, in recent years, for practical realization of the iterative approximation method, studies on reduction in calculation time and reduction in memory usage are in progress.

On the other hand, as a filtered back projection method in multi-slice CT, an expanded Feldkamp method or a method based on the expanded Feldkamp method is mainly used. According to this method, a reconstruction filter, such as a lamp filter or a Shelpp-Logan filter, is applied to projection data, and then a value is buried (integrated) in an image by a back projection process. As the back projection process, a ray-driven type, a pixel-driven or voxel-driven type, and a distance-driven type are known.

A distance-driven type will be simply described referring to FIG. 16.

The distance-driven type refers to a method in which the distance between a pixel boundary and a beam boundary is considered as a reference. In a back projection process of the distance-driven type, as shown in FIG. 16, when the distance between the pixel boundary and the beam boundary is scanned, a projection value is sequentially buried in pixels 104 included in a beam 102. The back projection process of the distance-driven type is disclosed in, for example, PTL 1.

In the iterative approximation method, an image which is generated by the filtered back projection method is used as an initial image, thereby achieving high-speed performance. Accordingly, even when image reconstruction is performed by the iterative approximation method, it is desirable to use the filtered back projection method in combination.

The above-described back projection process is also performed in an iterative process in the iterative approximation method. Accordingly, when the filtered back projection method and the iterative approximation method are used in combination, the back projection process of the same method is introduced, whereby it is possible to obtain a tomographic image with no difference concerning the back projection process and to achieve reduction in development cost.

In the X-ray CT apparatus, an offset (referred to as "quarter offset") for ¼ channel in a channel direction of a detector is made, and the beam paths of data having a target phase and data having an opposing phase are deviated. As a result, it is possible to effectively improve sampling density in the channel direction of the beam. In order to obtain a high-resolution image, it should suffice that a back projection process is performed from the nearest beam including opposing data. This method is referred to as high-resolution reconstruction. The high-resolution reconstruction is a technique which is useful for head scanning (in particular, diagnosis of a microstructure, such as an inner ear).

As high-resolution conversion, an opposing insertion method or a data interpolation method is generally used. The data interpolation method is disclosed in, for example, PTL 2 and PTL 3.

From above, even when image reconstruction is performed by the iterative approximation method, it is desirable to use the filtered back projection method in combination and to introduce the back projection process of the same method. It is desirable that the back projection process can perform high-resolution reconstruction.

CITATION LIST

Patent Literature

PTL 1: JP-T-2005-522304
PTL 2: JP-A-6-181919
PTL 3: JP-A-10-314161

SUMMARY OF INVENTION

Technical Problem

In the distance-driven type, it is possible to secure constant sampling density. When the pixel size is comparatively greater than the detector element size, this allows noise reduction. Since uniform back projection is possible, no high-frequency errors, such as moire, occur. Also, since continuity of data access is high, high-speed processing is possible.

However, as disclosed in FIG. 6 of PTL 1, in a mechanism in which the square window or the width of the shadow of the pixel is adjusted, these are constantly adjacent, the gap is removed, and these are actually continuous, there is a problem in that it is not possible to perform the above-described high-resolution reconstruction. This is because, when burying projection data having a target phase, projection data having an opposing phase is not taken into consideration.

The invention has been accomplished in consideration of the above-described problem, and an object of the invention is to provide an X-ray CT apparatus or the like capable of executing a high-resolution reconstructible distance-driven back projection process and generating a high-resolution tomographic image.

Solution to Problem

In order to attain the above-described object, the invention provides an image reconstruction method which is executed by an X-ray CT apparatus on the basis of parallel beam data obtained by fan-parallel conversion on fan beam data. The image reconstruction method includes setting parallel beam data having a phase to be processed as target data, setting parallel beam data having a phase opposing target data as opposing data, and determining the presence/absence of opposing data corresponding to target data, and performing different high-resolution reconstruction depending on the determination result, executing a back projection process on the basis of the distance between a pixel boundary and a beam boundary using target data or target data and opposing data, and performing image reconstruction.

Advantageous Effects of Invention

According to the invention, it is possible to provide an X-ray CT apparatus or the like capable of executing a high-resolution reconstructible distance-driven back projection process and generating a high-resolution tomographic image at high speed.

DESCRIPTION OF EMBODIMENTS

Figure 1:
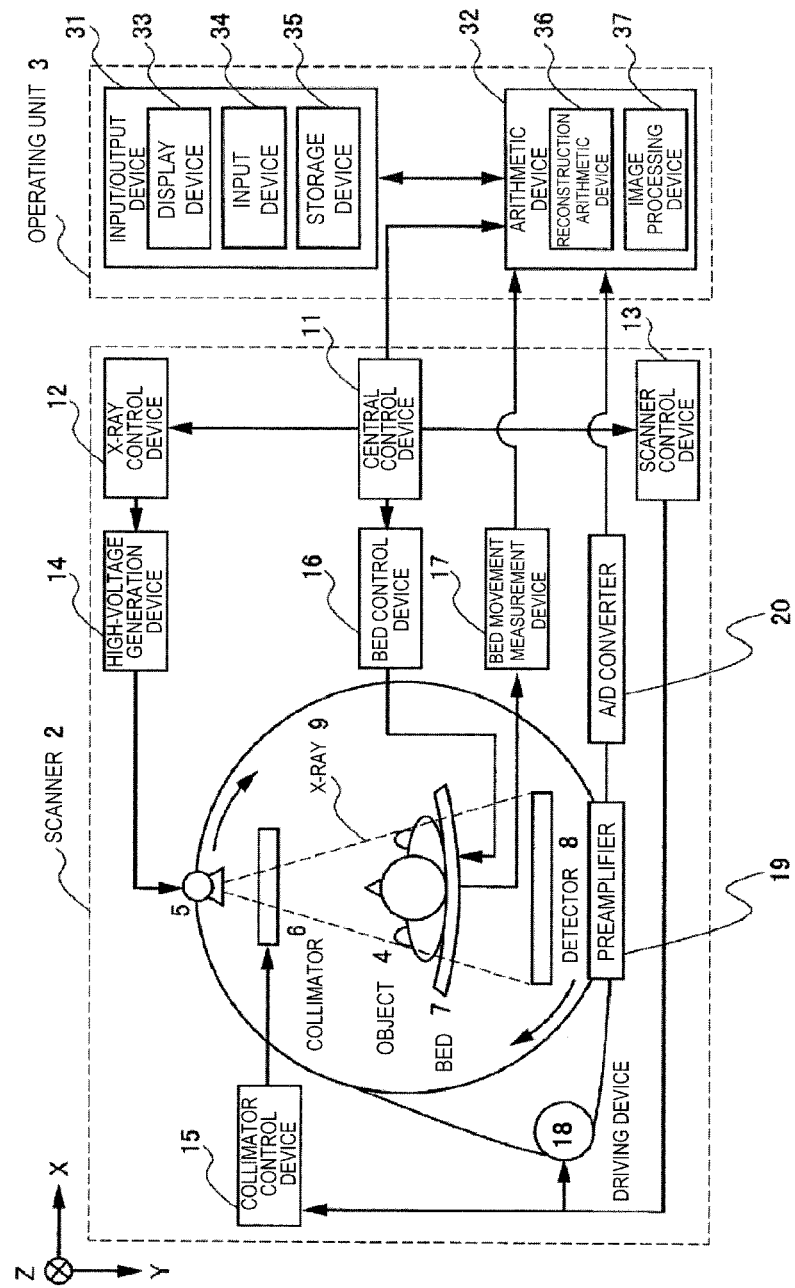
FIG. 1 is a configuration diagram of an X-ray CT apparatus.

An embodiment of the invention will be described.
The invention provides an X-ray CT apparatus which performs image reconstruction on the basis of parallel beam data obtained by fan-parallel conversion on fan beam data. The X-ray CT apparatus includes a determination unit which sets parallel beam data having a phase to be processed as target data, sets parallel beam data having a phase opposing target data as opposing data, and determines the presence/absence of opposing data corresponding to target data, and an image reconstruction unit which performs different high-resolution reconstruction depending on the determination result of the determination unit, executes a back projection process on the basis of the distance between a pixel boundary and a beam boundary using target data or target data and opposing data, and performs image reconstruction.

The X-ray CT apparatus further includes a decision unit which decides a window function representing a rate at which a projection value corresponding to target data or target data and opposing data contributes to a pixel value, wherein the image reconstruction unit applies the shape of the window function decided by the decision unit to execute back projection process.

When the determination unit determines that opposing data is present, the decision unit decides the shape of the window function relating to one of target data and opposing data is point symmetrical to the vertically inverted shape of the window function relating to the other one of target data and opposing data.

The decision unit sets the shape of the window function relating to target data and opposing data as rectangular shape.

The decision unit is able to select a triangular shape, a trapezoidal shape, and a rectangular shape as the shape of the window function relating to target data and opposing data.

The image reconstruction unit generates an initial image of an iterative process in an iterative approximation method by a filtered back projection process, and executes the iterative process in the iterative approximation method on the basis of the initial image.

The back projection process performs weighting of a pixel value in accordance with the distance between the pixel boundary and the beam boundary.

Another embodiment of the invention will be described.
The invention provides an image reconstruction method which is executed by an X-ray CT apparatus on the basis of parallel beam data obtained by fan-parallel conversion on fan beam data. The image reconstruction method includes a determination step of setting parallel beam data having a phase to be processed as target data, setting parallel beam data having a phase opposing target data as opposing data, and determining the presence/absence of opposing data corresponding to target data, and an image reconstruction step of performing different high-resolution reconstruction depending on the determination result in the determination step, executing a back projection process on the basis of the distance between a pixel boundary and a beam boundary using target data or target data and opposing data, and performing image reconstruction.

Next, the embodiments of the invention will be described in detail referring to the drawings.

In the following description and the accompanying drawings, the constituent elements having the same functions are represented by the same reference signs, and overlapping description will be omitted.

First, the configuration of an X-ray CT apparatus 1 will be described referring to FIG. 1.

The X-ray CT apparatus 1 is, for example, a multi-slice CT apparatus. A scan system is, for example, a rotate-rotate system (third generation). The X-ray CT apparatus 1 has a scanner 2, an operating unit 3, and a bed 7.

The scanner 2 performs a scan process of an object 4 placed on the bed 7 in accordance with an instruction by the operating unit 3.

The scanner 2 has an X-ray generation device 5, a collimator 6, a detector 8, a central control device 11, an X-ray control device 12, a scanner control device 13, a high-voltage generation device 14, a collimator control device 15, a bed control device 16, a bed movement measurement device 17, a driving device 18, a preamplifier 19, an A/D converter 20, and the like.

The operating unit 3 has an input/output device 31, an arithmetic device 32, and the like. The input/output device 31 includes a display device 33, an input device 34, a storage device 35, and the like. The arithmetic device 32 includes a reconstruction arithmetic device 36, an image processing device 37, and the like.

The input device 34 in the operating unit 3 has a mouse, a keyboard, a touch panel, or the like, and inputs measurement parameters and reconstruction parameters, such as bed movement speed information and reconstruction position. The display device 33 has a display device, such as a liquid crystal display.

The storage device 35 has a hard disk or drive devices of various storage mediums.

A user inputs scanning conditions (bed movement speed, tube current, tube voltage, slice position, and the like) or reconstruction conditions (reconstruction method, ON/OFF of high-resolution process, image slice thickness, back projection phase width, region of interest, reconstructed image matrix size, reconstruction filter function, maximum number of iterations of iterative approximation process, convergence conditions, and the like) from the input device 34 in the operating unit 3.

The central control device 11 sends control signals required for scanning to the X-ray control device 12, the scanner control device 13, and the bed control device 16 on the basis of an instruction to be input, receives an scanning start signal, and starts scanning.

If scanning starts, a control signal is sent to the high-voltage generation device 14 by the X-ray control device 12, a high voltage is applied to the X-ray generation device 5, and an X-ray 9 is irradiated onto the object 4 from the X-ray generation device 5. Simultaneously, a control signal is sent from the scanner control device 13 to the driving device 18, and a gantry in which the X-ray generation device 5, the detector 8, the preamplifier 19, and the like are mounted revolves around the object 4.

The bed 7 on which the object 4 is placed is stationary (during normal scan) or makes parallel movement (during spiral scan) in the body axis direction of the subject 4 in response to a control signal from the bed control device 16. The X-ray 9 has an irradiation region which is limited by the collimator 6, is absorbed (attenuated) in each tissue of the object 4, passes through the object 4, and is detected by the detector 8. The X-ray 9 which is detected by the detector 8 is converted to a current, the current is amplified by the preamplifier 19 and converted to digital data by the A/D converter 20, and digital data is subjected to LOG conversion and calibration and input to the arithmetic device 32 as a projection data signal.

The projection data signal which is input to the arithmetic device 32 becomes input data for an image reconstruction process which is performed by the reconstruction arithmetic device 36. A reconstructed image is stored in the storage device 35 and displayed as a CT image by the display device 33. Alternatively, the reconstructed image is subjected to image processing by the image processing device 37, and then displayed as a CT image by the display device 33.

The summary of a scanning process and an image reconstruction process by the X-ray CT apparatus 1 will now be described.

In the X-ray CT apparatus 1, a tube voltage and a tube current are applied to an X-ray tube serving as the X-ray generation device 5 on the basis of the scanning conditions which are input from the input device 34 of the operating unit 3 connected to the scanner 2.

In the X-ray CT apparatus 1, electron having energy according to the applied tube voltage is emitted from the cathode, and the emitted electron collides against a target (anode), whereby the X-ray 9 having energy according to electron energy is irradiated from the X-ray source of the X-ray tube. The irradiated X-ray 9 transmits through the object 4, and the X-ray 9 which is attenuated in accordance with an X-ray attenuation coefficient of a substance (tissue) in the object 4 is received by the detector 8 which is arranged at a position facing the X-ray source, thereby obtaining projection data.

In a case of a filtered back projection method, the reconstruction arithmetic device 36 of the X-ray CT apparatus 1 superimposes a reconstruction filter on projection data to obtain filtered projection data, and performs back projection (image reconstruction) on filtered projection data while weighting the weight (hereinafter, referred to as "view weight") of the substantially same shape in the view direction which is decided under the scanning conditions and does not depend on the position of the tomographic image, whereby the tomographic image is imaged non-destructively as a distribution chart of the X-ray attenuation coefficient inside the object 4.

In regard to the detector 8 of the X-ray CT apparatus 1, for the purpose of scanning a wide range in a short time, a two-dimensional detector (also referred to as "multiseriate detector" or "multi-slice detector") in which a one-dimensional detector (also referred to as "uniseriate detector" or "single slice") is arranged one-dimensionally in the revolution direction is expanded in the revolution axis direction may be used. In general, the X-ray CT apparatus 1 in which the detector 8 is arranged one-dimensionally in the revolution direction is referred to as "single slice CT", and the X-ray CT apparatus 1 in which the detector 8 is arranged two-dimensionally is referred to as "multi-slice CT". In the single slice CT, an X-ray beam which expands in a fan shape from the X-ray generation device 5 (X-ray source) is irradiated, and in the multi-slice CT, an X-ray beam which expands in a conical shape or a pyramid shape from the X-ray generation device 5 (X-ray source) in conformity with the detector 8 is irradiated.

In the X-ray CT apparatus 1, X-ray irradiation is performed while revolving around the subject 4 placed on the bed 7. At this time, scanning in which the bed 7 is fixed and the X-ray generation device 5 (X-ray source) revolves around the subject 4 in a circular orbit shape is referred to as "normal scan", "axial scan", or the like. Scanning in which the bed 7 moves and the X-ray generation device 5 (X-ray source) revolves around the subject 4 in a spiral orbit shape is referred to as "spiral scan", "helical scan", or the like.

In an iterative approximation method, the X-ray CT apparatus 1 has an advantage for high-speed performance in that an image which is generated by the filtered back projection method is used as an initial image. During an iterative process in the iterative approximation method, it is advantageous that the X-ray CT apparatus 1 applies a distance-driven back projection process for the reason of frequency error or the like. High-resolution reconstruction is performed on the basis of the distance-driven back projection process, during the iterative process of the filtered back projection method and the iterative approximation method, the back projection process of the same system can be applied. Accordingly, it is possible to obtain a tomographic image with no difference concerning the back projection process and to achieve reduction in development cost.

Next, a need for fan-parallel conversion in the embodiments of the invention will be described referring to FIGS. 2 and 3.

Figure 2:
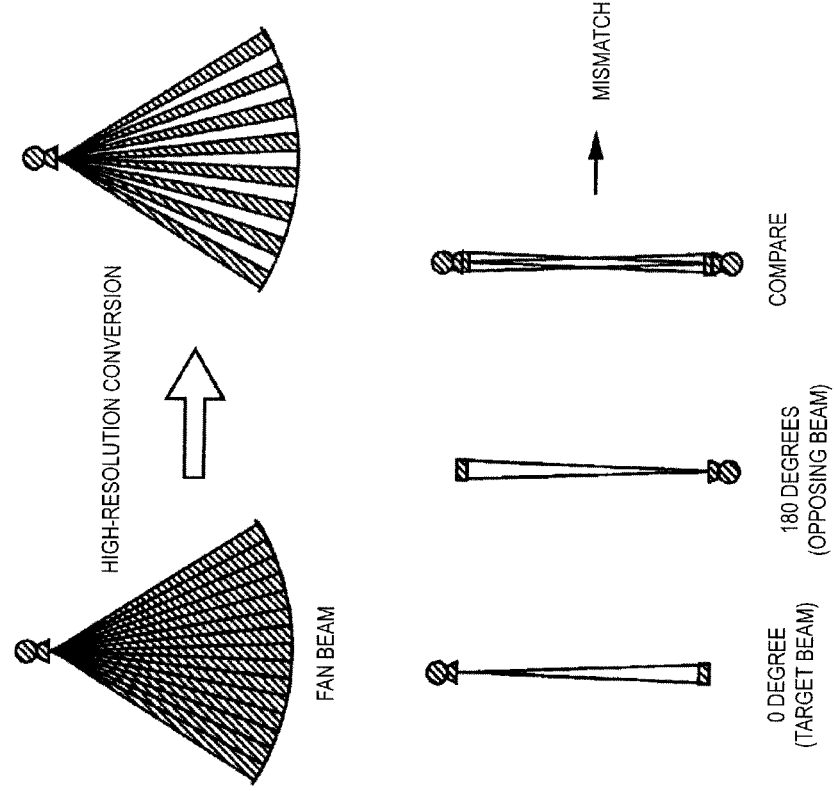
FIG. 2 is a comparison diagram of the shapes of a target beam and an opposing beam in a fan beam.

As shown in FIG. 2, a fan beam has a fan-shaped expanse when viewed from the revolution axis direction. In the case of a fan beam, during the distance-driven back projection process, one beam is regarded as a triangular shape. In this case, when comparing the shapes of a target beam and an opposing beam, as shown in FIG. 2, the shapes of both are different from each other. For this reason, it is not possible to perform high-resolution reconstruction using data relating to the opposing beam in addition to the target beam.

Figure 3:
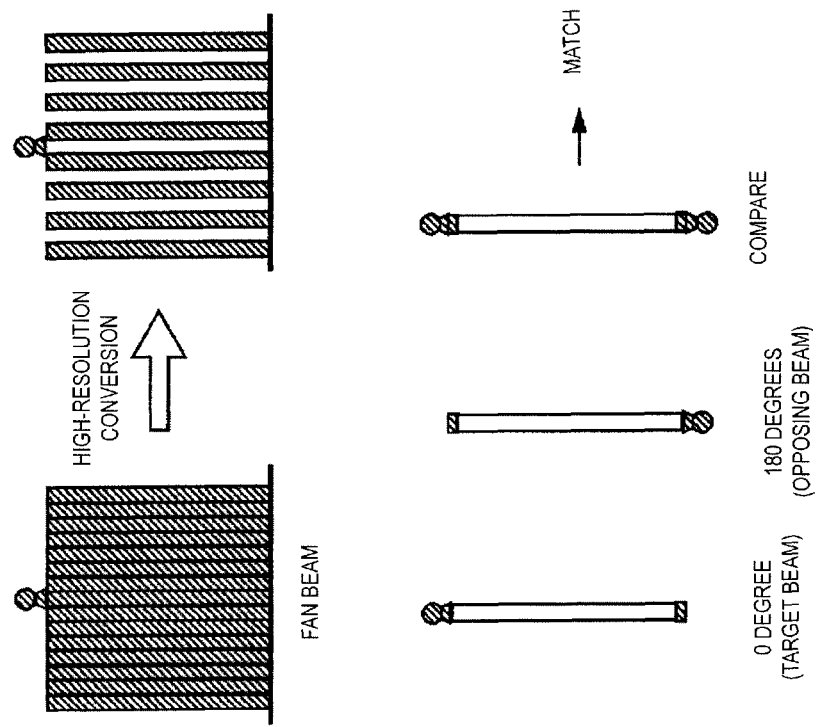
FIG. 3 is a comparison diagram of the shapes of a target beam and an opposing beam in a parallel beam.

Meanwhile, as shown in FIG. 3, a parallel beam is in parallel when viewed from the revolution axis direction and has a regular interval. In the case of a parallel beam, during the distance-driven back projection process, one beam is regarded as a rectangular shape. In this case, when comparing the shapes of a target beam and an opposing beam, as shown in FIG. 3, the shapes of both are identical. For this reason, data relating to the opposing beam is used by a "zero-insertion method" described below, and high-resolution reconstruction can be performed.

Accordingly, the reconstruction arithmetic device 36 performs fan-parallel conversion which is a conversion process from fan beam data to parallel beam data, and performs an image reconstruction process on the basis of parallel beam data after fan-parallel conversion. For the fan-parallel conversion process, known techniques may be used.

Hereinafter, it is assumed that parallel beam data having a phase to be processed is target data, and parallel beam data having a phase opposing target data is opposing data.

Next, the back projection process in the embodiments of the invention will be described referring to FIGS. 4 to 6. In regard to the processes other than the back projection process, known techniques may be used, thus description will be omitted.

The reconstruction arithmetic device 36 of the X-ray CT apparatus 1 uses the filtered back projection method and the iterative approximation method together, and introduces the distance-driven back projection process. In the filtered back projection method, the reconstruction arithmetic device 36 executes a first back projection process shown in FIG. 4. In the iterative approximation method, the reconstruction arithmetic device 36 executes the first back projection process shown in FIG. 4 or a second back projection process shown in FIG. 5. In the iterative approximation method, the reconstruction arithmetic device 36 repeatedly executes the back projection process.

First, a case where the reconstruction arithmetic device 36 executes the first back projection process shown in FIG. 4 by the filtered back projection method will be described.

The reconstruction arithmetic device 36 determines the presence/absence of opposing data corresponding to each piece of target data on the basis of scanning conditions, and calculates a phase range where opposing data is present (Step 11). That is, the reconstruction arithmetic device 36 calculates a back projection phase width which can be used to generate one slice of reconstructed image from the scanning conditions.

Specifically, the reconstruction arithmetic device 36 calculates the back projection phase width from parallel beam data in the following manner in reconstruction taking into consideration an X-ray beam gradient in the body axis direction like Feldkamp reconstruction.

$$F \leq \frac{\Delta d_{row} \cdot (N_{row} - 1) \cdot \left(SID - \frac{FOM}{2}\right)}{T \cdot SDD} - \frac{2 \cdot \arcsin\left(\frac{FOM}{2 \cdot SID}\right)}{T} \quad (1)$$

$$FOM = FOV + 2 \cdot \sqrt{x_0^2 + y_0^2} \text{ or } \sqrt{(FOV_x + 2x_0)^2 + (FOV_y + 2y_0)^2} \quad (2)$$

Here, F denotes a back projection phase width, $\Delta d_{row}$ denotes a column-direction detector element size, $N_{row}$ denotes the number of detector columns, SID denotes the distance between a radiation source and a revolution center, T denotes a bed movement speed, SDD denotes the distance between a radiation source and a detector, FOV denotes an effective field-of-view size, $x_0$ denotes the reconstruction center position in the X direction, $y_0$ denotes the reconstruction center position in the Y direction, $FOV_x$ denotes the FOV size in the X direction, and $FOV_y$ denotes the FOV size in the Y direction. Although the back projection phase width is calculated from the scanning conditions using the above expressions, the invention is not limited thereto, and the back projection phase width which has been calculated in advance may be used or may be directly set from the input device as the reconstruction conditions. Assuming that projection data is expanded in the detector column direction by extrapolation, the back projection phase width may be set to be greater than a value which is calculated from the above expressions.

Figure 6:
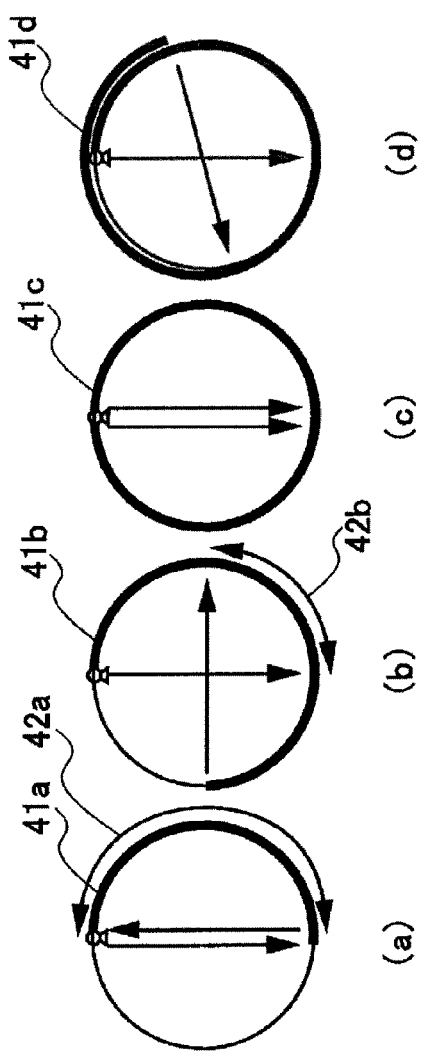
FIG. 6 is a diagram showing the relationship between a back projection phase width and presence/absence of opposing data.

FIG. 6 shows the relationship between a back projection phase width and the presence/absence of opposing data. 41a, 41b, 41c, and 41d represent a back projection phase width. 42a and 42b represent a phase in which no opposing data is present.

FIG. 6(a) shows an example of a case where the back projection phase width is 180 degrees, FIG. 6(b) shows an example of a case where the back projection phase width is 180 degrees to 360 degrees, FIG. 6(c) shows an example of a case where the back projection phase width is 360 degrees, and FIG. 6(d) shows an example of a case where the back projection phase width is equal to or greater than 360 degrees.

As shown in FIG. 6(a), when the back projection phase width 41a is 180 degrees, the phase 42a in which no opposing data is present ranges over 180 degrees, and no opposing data is present in all phases.

As shown in FIG. 6(b), when the back projection phase width 41b is 270 degrees, the phase 42b in which no opposing data is present ranges over 90 degrees.

As shown in FIG. 6(c), when the back projection phase width 41c is 360 degrees, the phase in which no opposing data is present ranges over 0 degree, and opposing data is present in all phases. The same applies to a case of FIG. 6(d).

Returning to the description of FIG. 4, the reconstruction arithmetic device 36 performs high-resolution conversion of a zero-insertion method (see FIG. 8) described below on a phase range where opposing data is present, and performs high-resolution conversion using a data interpolation method (see FIG. 9) described below on a phase range where no opposing data is present. The reconstruction arithmetic device 36 creates double sampled high-resolution projection data (Step 12). In the case of a single slice CT, high-resolution conversion of an opposing insertion method (see FIG. 7) described below may be performed on a phase range where opposing data is present.

The reconstruction arithmetic device 36 calculates the view weight (Step 13), and performs a filter correction process on high-resolution projection data. The reconstruction arithmetic device 36 performs a distance-driven back projection process (see FIG. 11) described below using filtered high-resolution projection data subjected to the filter correction, and generates a reconstructed image (Step 14).

Next, a case where the reconstruction arithmetic device 36 executes the first back projection process shown in FIG. 4 by the iterative approximation method will be described.

The reconstruction arithmetic device 36 determines the presence/absence of opposing data corresponding to each piece of target data on the basis of the scanning conditions and calculates a phase range where opposing data is present (Step 11).

Figure 4:
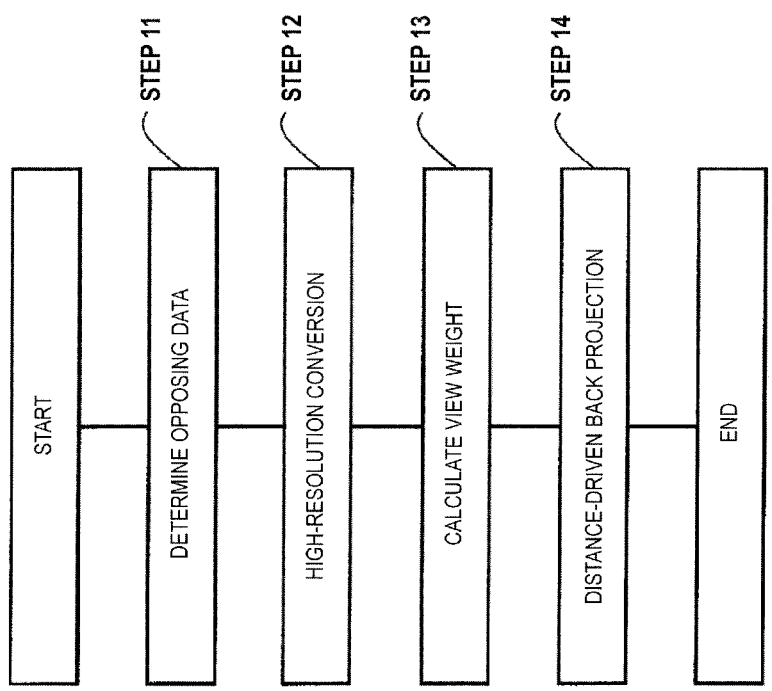
FIG. 4 is a flowchart showing the flow of a first back projection process.

According to the method of the first back projection process shown in FIG. 4, after the presence/absence of opposing data is determined (Step 11), in the back projection process during the iterative process when an image is generated by the iterative approximation reconstruction method, the reconstruction arithmetic device 36 performs high-resolution conversion using the zero-insertion method on a phase range where opposing data of parallel beam projection data is present, and performs high-resolution conversion using the data interpolation method on a phase range where no opposing data is present, thereby creating double sampled parallel/high-resolution projection data (Step 12). Then, the reconstruction arithmetic device 36 calculates the view weight (Step 13), and performs distance-driven back projection of parallel/high-resolution projection data to generate an image (Step 14).

According to another method of the first back projection process shown in FIG. 4, after the presence/absence of opposing data is determined (Step 11), in the back projection process during the iterative process when an image is generated by the iterative approximation reconstruction method, the reconstruction arithmetic device 36 performs high-resolution conversion using the data interpolation method when opposing data of parallel beam projection data is present and when no opposing data is present (Step 12), thereby obtaining parallel/high-resolution projection data. Then, the reconstruction arithmetic device 36 calculates the view weight (Step 13), and performs the distance-driven back projection process (Step 14).

Next, a case where the reconstruction arithmetic device 36 executes the second back projection process shown in FIG. 5 by the iterative approximation method will be described.

The reconstruction arithmetic device 36 determines the presence/absence of opposing data corresponding to each piece of target data on the basis of the scanning conditions, and calculates a phase range where opposing data is present (Step 21).

Figure 5:
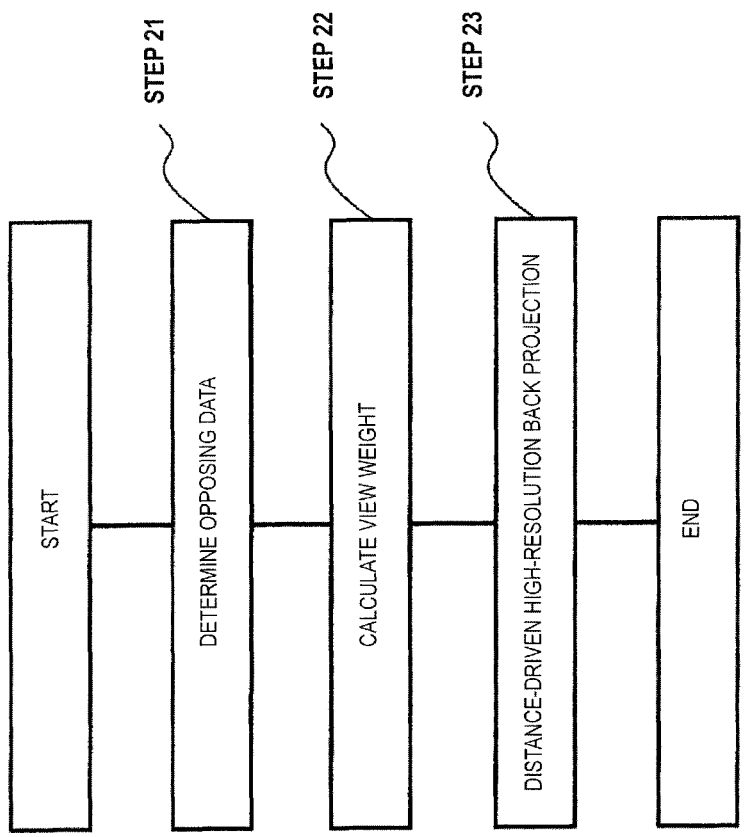
FIG. 5 is a flowchart showing the flow of a second back projection process.

According to the method of the second back projection process shown in FIG. 5, after the presence/absence of opposing data is determined (Step 21), in the back projection process during the iterative process when an image is generated by the iterative approximation reconstruction method, the reconstruction arithmetic device 36 calculates the view weight (Step 22), and performs the distance-driven high-resolution back projection process, in which the window dimension of the detector element with respect to one of the pixel and the detector element is set to half the size when no opposing data is present, on a phase range where opposing data of parallel beam projection data is present, thereby generating an image (Step 23). In the case of a single slice CT, high-resolution conversion of an opposing insertion method (see FIG. 7) described below may be performed on a phase range where opposing data is present.

It is desirable that the initial image which is the input mage for the iterative process is generated by the filtered back projection process. Accordingly, it is possible to reduce the calculation time of the iterative process.

Next, three methods of high-resolution conversion will be described referring to FIGS. 7 to 9. The three methods are an opposing insertion method, a zero-insertion method, and a data interpolation method.

In the X-ray CT apparatus 1, an offset ("quarter offset") for ¼ channel is made in the channel direction of the detector 8. Projection data which is obtained by the quarter offset is reconstructed taking into consideration opposing data, whereby a high-resolution image can be obtained.

In order to perform high-resolution reconstruction using the quarter offset, opposing data should be present. Although in an axial scan of a single slice CT, opposing data is constantly present, in a spiral scan of a multi-slice CT, if Feldkamp reconstruction is performed, a usable view width is limited, and opposing data is present only in some phases. Specifically, when the bed movement speed is low, since the phase width (view width) which is usable for back projection is collected for 360 degrees, opposing data is present in all phases. When the bed movement speed is high, since the phase width which is usable for back projection is not collected for 360 degrees, opposing data is present only in some phases.

In general, only when the phase width at which back projection is possible is collected for equal to or greater than 360 degrees and opposing data is present in all phases, high-resolution reconstruction is performed. In the embodiments of the invention, even when the phase width at which back projection is possible is not collected for 360 degrees and opposing data is present only in some phases, a process in which a high-resolution image is obtained is executed as much as possible.

(1) Opposing Insertion Method

The opposing insertion method is a method in which, for example, projection data for 360 degrees is prepared, and opposing data is buried (inserted) in target data, thereby generating projection data for 180 degrees having double the number of channels and half the channel interval. The X-ray CT apparatus 1 performs a filter correction process assuming that double sampled projection data which is obtained by the opposing insertion method is obtained by a virtual detector having double the number of channels, thereby obtaining filtered projection data. Then, the X-ray CT apparatus 1 buries projection data for 180 degrees in the pixel (performs back projection) while generating a beam passing through the pixel center on the basis of filtered projection data by interpolation between the nearest beams, thereby obtaining a high-resolution image. When this method is used, sampling is effectively doubled, and an interpolation between nearer pieces of projection data including opposing data is possible, whereby a high-resolution image can be generated. In the filtered back projection method, data is double sampled in the channel direction before the filter correction process, and a reconstruction filter which is more suitable for high-frequency characteristics is used, thereby achieving high-resolution.

Figure 7:
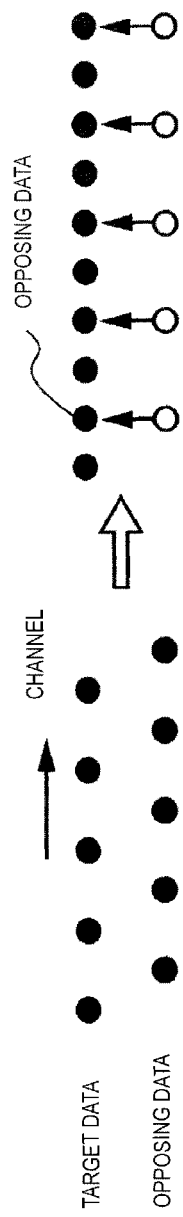
FIG. 7 is a diagram showing opposing insertion method.

Specifically, as shown in FIG. 7, the reconstruction arithmetic device 36 inserts opposing data between the corresponding channels of each piece of target data (hereinafter, referred to as "opposing insertion") to double density sampling in the channel direction. Thereafter, 180-degree back projection is performed. In the opposing insertion method, since opposing data is required, the opposing insertion method can be applied only to a phase range where opposing data is present. For this reason, in the case of a spiral scan, a comparatively low-speed spiral pitch should be used. Since it should suffice that back projection is performed for 180 degrees, a high-speed reconstruction process is achieved.

In the case of projection data which is obtained by the multi-slice CT, since opposing data (the column position of projection data) changes between the pixels, it is not possible to perform opposing insertion. For this reason, the opposing insertion method can be used only in the single slice CT. In the opposing insertion method, since there is projection data for 180 degrees during back projection, the reconstruction arithmetic device 36 performs the back projection process without using the view weight.

(2) Zero-Insertion Method

Figure 8:
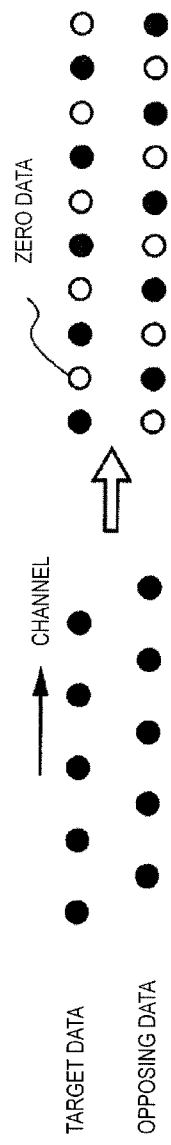
FIG. 8 is a diagram showing a zero-insertion method.

In the zero-insertion method, as shown in FIG. 8, the reconstruction arithmetic device 36 inserts zero data between the channels instead of opposing data (hereinafter, referred to as "zero-insertion") to achieve high-density sampling in the channel direction, and performs back projection for the same back projection phase width as the normal reconstruction process. In the zero-insertion method, since opposing data is required, the zero-insertion method can be applied only to a phase range where opposing data is present.

In the zero-insertion method, unlike the opposing insertion method, since zero is merely inserted between the channels, the zero-insertion method can also be applied to projection data which is obtained by the multi-slice CT. In the zero-insertion method, when the back projection phase width is equal to or smaller than 360 degrees, the view weight should be set to 1 during back projection ("1" is equivalent to a case where no view weight is used) or reconstruction should be performed without using the view weight. When the back projection phase width is equal to or greater than 360 degrees, a known view weight can be used. With the use of the view weight, it is possible to reduce a motion artifact due to the motion of the subject or a helical artifact due to a spiral scan.

(3) Data Interpolation Method

The data interpolation method is a method in which, for example, projection data for 360 degrees is prepared, and data created from projection data having a target phase by interpolation is buried to achieve double sampling. The X-ray CT apparatus 1 generates projection data for 360 degrees having double the number of channels and half the channel interval by the data interpolation method, and assuming that projection data is obtained by a virtual detector having double the number of channels, buries projection data for 360 degrees in the pixel (performs back projection) while generating a beam passing through the pixel center by interpolation between the nearest beams, thereby obtaining a high-resolution image.

Figure 9:
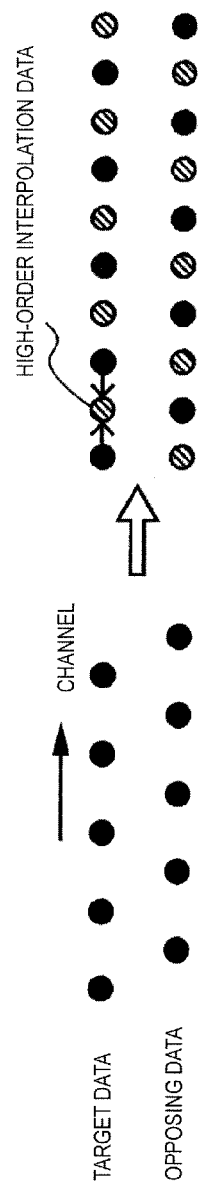
FIG. 9 is a diagram showing a data interpolation method.

Specifically, as shown in FIG. 9, the reconstruction arithmetic device 36 performs an interpolation process between the channels in the same phase to double densify sampling, and performs back projection for the back projection phase width. The data interpolation method can be applied even if there is no opposing data, and in the case of a spiral scan, a comparatively high-speed spiral pitch can be used. In the data interpolation method, similarly to the zero-insertion method, since interpolation data is merely inserted between the channels, the data interpolation method can also be applied to projection data which is obtained by the multi-slice CT, and during back projection, a known view weight can be used regardless of the back projection phase width.

In the data interpolation method, since high-density sampling is achieved by interpolation between the pieces of target data, spatial resolution is inferior compared to the opposing insertion method or the zero-insertion method.

Next, the distance-driven back projection process in Step 14 of FIG. 4 and the distance-driven high-resolution back projection process in Step 23 of FIG. 5 will be described referring to FIGS. 10 to 15.

Figure 10:
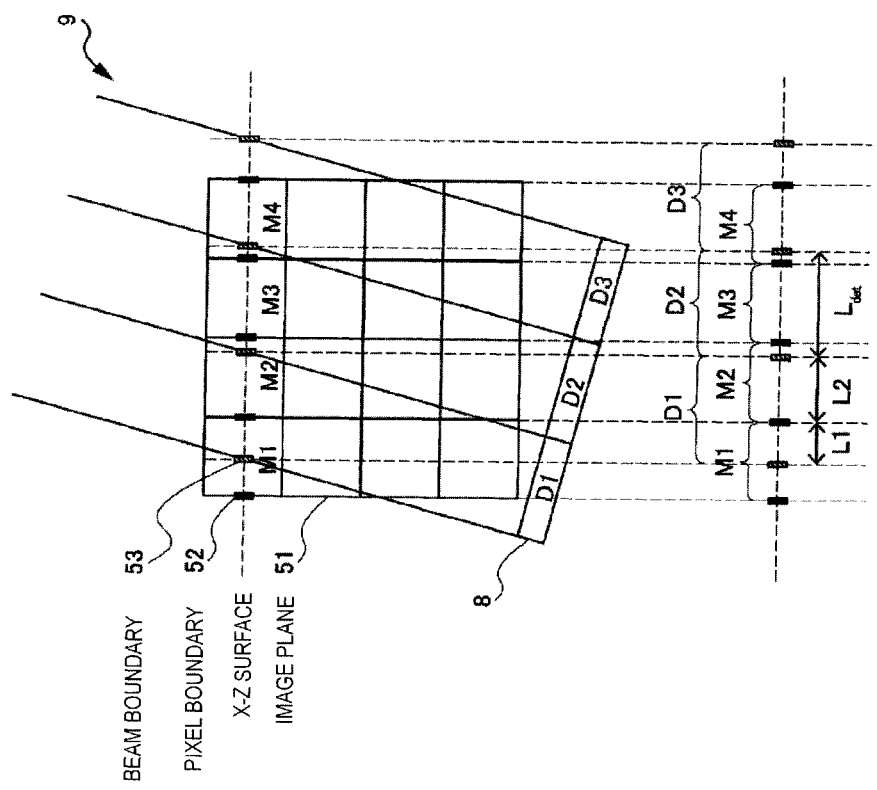
FIG. 10 is an explanatory view of a distance-driven back projection process.

FIG. 10 shows the locus of the X-ray 9 with respect to an image plane 51 which represents an aggregate of pixels when the object 4 is viewed from the side. Specifically, the locus until the X-ray 9 starts from the X-ray generation device 5, passes through the image plane 51, and reaches the detector 8 is shown.

A pixel boundary 52 represents a boundary position between adjacent pixels (M1, M2, M3, and M4) in the X-axis direction on the X-Z surface.

A beam boundary 53 represents a boundary position of a virtual X-ray beam. The beam boundary 53 matches a boundary position between adjacent detector elements (D1, D2, and D3) in the X-axis direction on the X-Z surface from the detector elements in the detector 8. The beam boundary 53 is a virtual boundary position for dividing the flux of an X-ray beam into each detector element for convenience of processing.

$L_{det}$ denotes the interval between the image boundaries 52, that is, the size of a detector element in the X-axis direction. Normally, $L_{det}$ is constant for all detector elements.

L1 denotes the width in the X-axis direction at which an X-ray beam corresponding to the detector element D1 and the pixel M1 overlap each other on the X-Z surface. Similarly, L2 denotes the width in the X-axis direction at which an X-ray beam corresponding to the detector element D1 and the pixel M2 overlap each other on the X-Z surface.

If a simplified form is considered, the following relationship is established.

detector element $D1$ projection value=($M1$ pixel value×$L1$+$M2$ pixel value×$L2$)/$L_{det}$ FIGS. 11 to 14 show different window functions.

In general, a window function is a function which becomes zero other than a certain finite interval. A window function is used so as to cut a specific shape in a finite space from an infinitely continuous space. In the embodiments of the invention, the window function means the ratio (contribution ratio) at which projection contributes to the pixel or vice versa.

The reconstruction arithmetic device 36 decides a window function, which represents the ratio of the projection value corresponding to target data contributing to the pixel value, in the first back projection process. The reconstruction arithmetic device 36 decides a window function, which represents the ratio of the projection values corresponding to target data and opposing data contributing to the pixel value, in the second back projection process.

Figure 11:
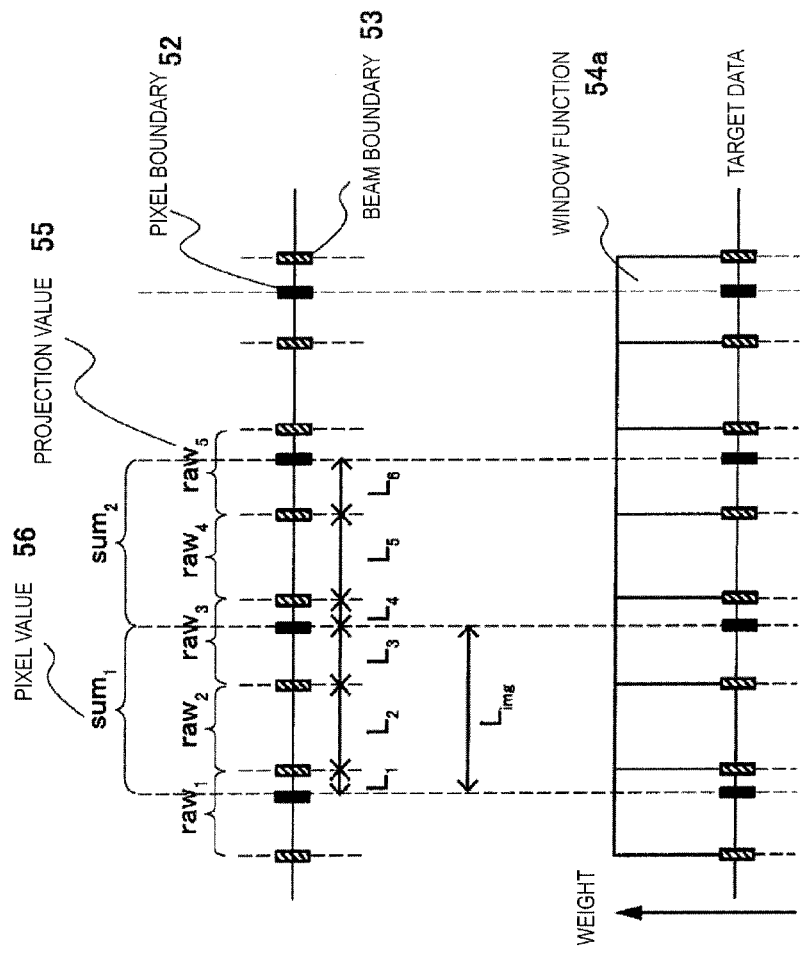
FIG. 11 is a diagram showing a window function of the related art.

FIG. 11 shows a window function in the first back projection process. The shape of a window function 54a shown in FIG. 11 is a rectangular shape, and is continuous with an adjacent window function 54a. That is, the horizontal width of the window function 54a is equal to the horizontal width of the beam boundary 53.

In the example shown in FIG. 11, the reconstruction arithmetic device 36 integrates the projection value of the X-ray beam included in the pixel boundary 52.

$raw_1$ to $raw_5$ are projection values 55 for the respective detector elements. $sum_1$ and $sum_2$ are pixel values 56 for the respective pixels.

$L_1$ denotes the width in the X-axis direction at which the window function 54a cutting out the projection value 55 "$raw_1$" and the pixel corresponding to pixel value 56 "$sum_1$" overlap each other on the X-Z surface. $L_2$ denotes the width in the X-axis direction at which the window function 54a cutting out the projection value 55 and the pixel corresponding to the pixel value 56 "$sum_1$" overlap each other on the X-Z surface. $L_3$ denotes the width in the X-axis direction at which the window function 54a cutting out the projection value 55 "$raw_3$" and the pixel corresponding to the pixel value 56 "$sum_1$" overlap each other on the X-Z surface.

$L_4$ denotes the width in the X-axis direction at which the window function 54a cutting out the projection value 55 "$raw_3$" and the pixel corresponding to the pixel value 56 "$sum_2$" overlap each other on the X-Z surface. $L_5$ denotes the width in the X-axis direction at which the window function 54a cutting out the projection value 55 "$raw_4$" and the pixel corresponding to the pixel value 56 "$sum_2$" overlap each other on the X-Z surface. $L_6$ denotes the width in the X-axis direction at which the window function 54a cutting out the projection value 55 "$raw_5$" and the pixel corresponding to the pixel value 56 "$sum_2$" overlap each other on the X-Z surface.

In the first back projection process, the reconstruction arithmetic device 36 performs the back projection process by applying the shape of the window function 54a shown in FIG. 11 and sequentially burying the projection value in the pixels of target data on the basis of the distance between the pixel boundary and the beam boundary, and performs image reconstruction.

For example, the reconstruction arithmetic device 36 executes the back projection process relating to the pixel value 56 "$sum_1$" by the following expression.

$$sum_1 = (raw_1 \times L_1 + raw_2 \times L_2 + raw_3 \times L_3)/L_{img}$$

For example, the reconstruction arithmetic device 36 executes the back projection process relating to the pixel value 56 "$sum_2$" by the following expression.

$$sum_2 = (raw_3 \times L_3 + raw_4 \times L_5 + raw_5 \times L_6)/L_{img}$$

In more general, the reconstruction arithmetic device 36 may use the area ratio as a weight instead of the width ratio in the X-axis direction.

That is, the reconstruction arithmetic device 36 may define the height of the window function 54a as d, $S_1 = d \times L_1, \ldots,$ and $S_6 = d \times L_6$, and may execute the back projection process relating to the pixel value 56 "$sum_1$" by the following expression.

$$sum_1 = (raw_1 \times S_1 + raw_2 \times S_2 + raw_3 \times S_3)/(S_1 + S_2 + S_3)$$

The reconstruction arithmetic device 36 may execute the back projection process relating to the pixel value 56 "$sum_2$" by the following expression.

$$sum_2 = (raw_3 \times S_4 + raw_4 \times S_5 + raw_5 \times S_6)/(S_4 + S_5 + S_6)$$

Figure 12:
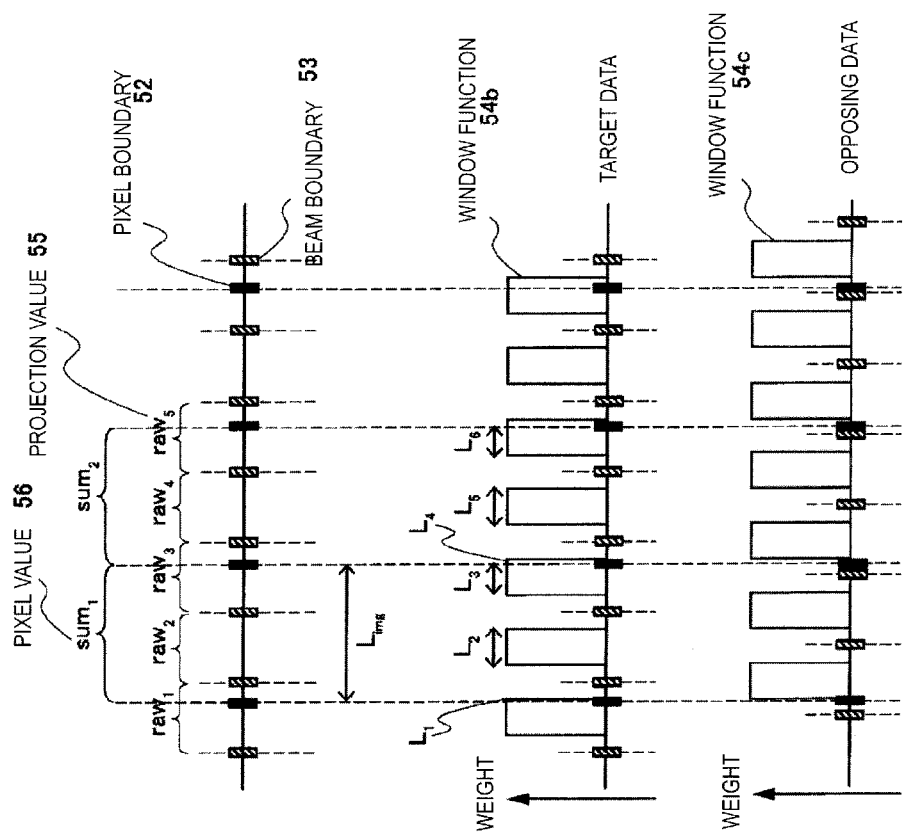
FIG. 12 is a diagram showing a rectangular window function.

FIG. 12 shows a first example of a window function in the second back projection process. A window function 54b shown in FIG. 12 relates to target data, and a window function 54c relates to opposing data. The shapes of the window functions 54b and 54c are rectangular shapes, and have the width which is half the width of the window function 54a shown in FIG. 11. Accordingly, the window functions 54b and 54c are not continuous with adjacent window functions 54b and 54c, respectively. The window functions 54b and the window function 54c have the same shape.

In the example shown in FIG. 12, the reconstruction arithmetic device 36 defines the shapes of the window functions 54b and 54c as a rectangular shape having a width half the width of the window function 54a, and sets the positions of the window functions 54b and 54c at the center of the X-ray beam (the window functions 54b and 54c are positioned such that the middle points in the width direction of the window functions 54b and 54c match the center of the X-ray beam). The reconstruction arithmetic device 36 multiplies the projection value 55 by the area ratios of the window functions 54b and 54c included in the pixel boundary 52 to the entire pixels as a weight, and further multiplies the projection value 55 by the view weight, thereby performing an integration process of projection data on the target pixel. The calculation method using the area ratio as a weight is the same as the calculation method described in the example shown in FIG. 11.

Figure 13:
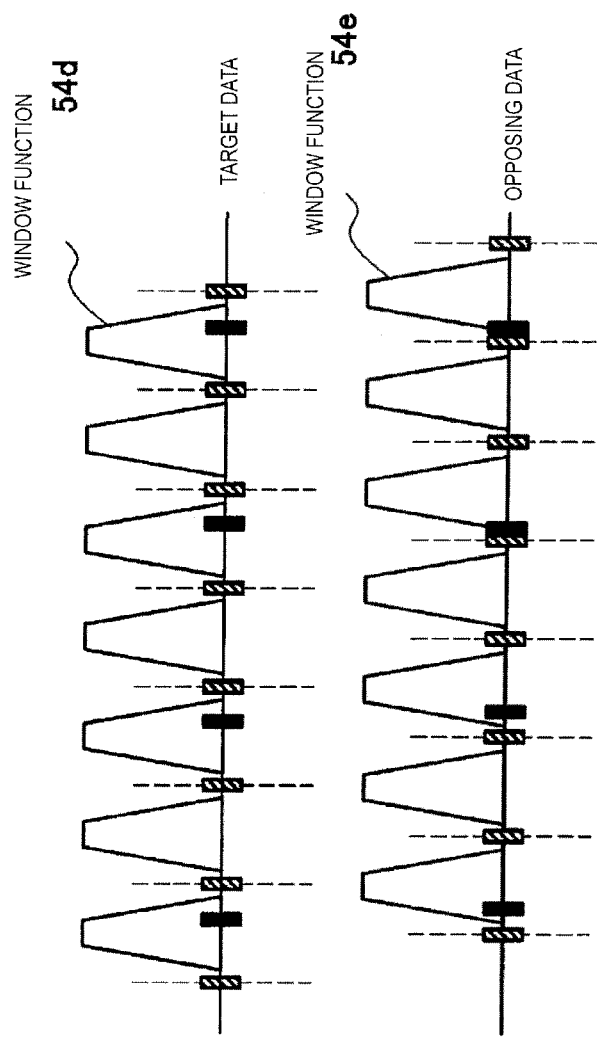
FIG. 13 is a diagram showing a trapezoidal window function.

FIG. 13 shows a second example of a window function in the second back projection process. A window function 54d shown in FIG. 13 relates to target data, and a window function 54e relates to opposing data. The shapes of the window functions 54d and 54e are isosceles trapezoidal shapes, and have an area half the area of the window function 54a shown in FIG. 11. Accordingly, the window functions 54d and 54e are not continuous with adjacent window functions 54d and 54e, respectively. The window function 54d and the window function 54e have the same shape.

In the example shown in FIG. 13, the reconstruction arithmetic device 36 defines the shapes of the window functions 54d and 54e as an isosceles trapezoidal shape having an area half the area of the window function 54a, and sets the positions of the window functions 54d and 54e at the center of the X-ray beam (the window functions 54d and 54e are positioned such that the middle points in the width direction of the window functions 54d and 54e match the center of the X-ray beam). The reconstruction arithmetic device 36 multiplies the projection value by the area ratios of the window functions 54d and 54e included in the pixel boundary 52 to the entire pixels as a weight, and further multiplies the projection value 55 by the view weight, thereby performing an integration process of projection data on the target pixel. The calculation method using the area ratio as a weight is the same as the calculation method described in the example shown in FIG. 11.

Figure 14:
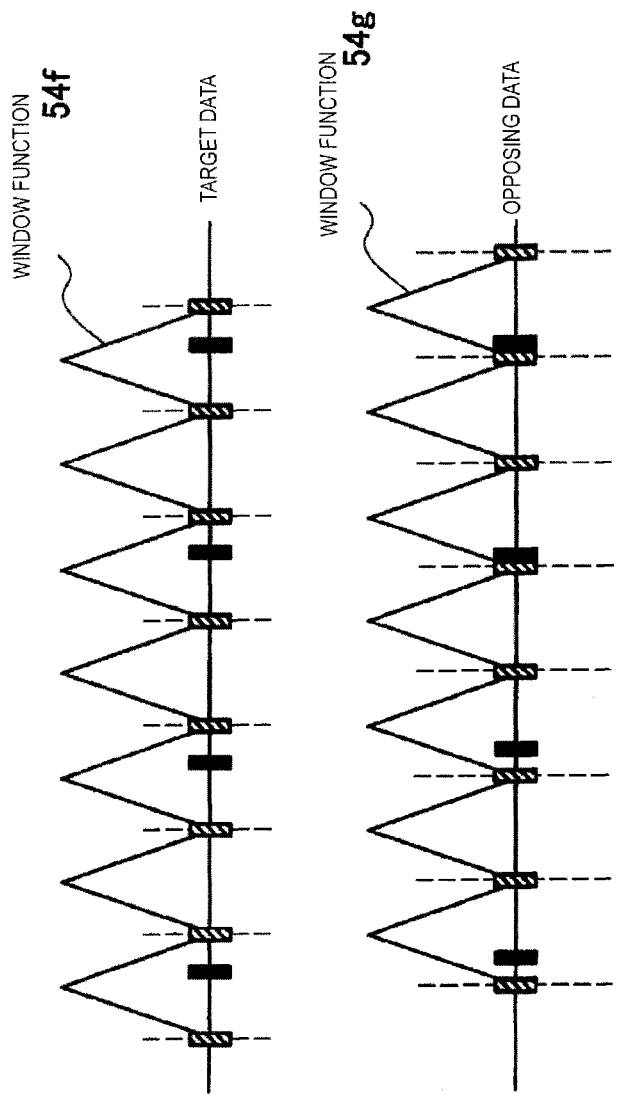
FIG. 14 is a diagram showing a triangular window function.

FIG. 14 shows a third example of a window function in the second back projection process. A window function 54f shown in FIG. 14 relates to target data, and a window function 54g relates to opposing data. The shapes of the window functions 54f and 54g are isosceles triangular shapes, and have an area half the area of the window function 54a shown in FIG. 11. Accordingly, the window functions 54f and 54g are respectively continuous with adjacent window functions 54f and 54g only at both apexes of the base. The window function 54f and the window function 54g have the same shape.

In the example shown in FIG. 14, the reconstruction arithmetic device 36 defines the shapes of the window functions 54f and 54g as an isosceles triangular shape having an area half the area of the window function 54a, and sets the positions of the window functions 54f and 54g at the center of the X-ray beam (the window functions 54f and 54g are positioned such that the middle points of the bases of the window functions 54f and 54g match the center of the X-ray beam). The reconstruction arithmetic device 36 multiplies the projection value by the area ratio of the window functions 54f and 54g included in the pixel boundary 52 to the entire pixels as a weight, and further multiples the projection value 55 by the view weight, thereby performing an integration process of projection data on the target pixel. The calculation method using the area ratio as a weight is the same as the calculation method described in the example shown in FIG. 11.

Hereinafter, when the window functions are collectively referred to, the window functions are represented by reference sign "54".

In the example (first back projection process) shown in FIG. 11, adjacent window functions 54 are continuous at all points of the beam boundary 53, and burying of opposing data is not taken into consideration. In the examples (second back projection process) shown in FIGS. 12 to 14, adjacent window functions 54 are discontinuous in the beam boundary 53 or are continuous only at one point, and burying of opposing data is taken into consideration. Accordingly, in the examples (second back projection process) shown in FIGS. 12 to 14, it becomes possible to perform high-resolution reconstruction using opposing data even in the distance-driven back projection process.

In particular, in the example shown in FIG. 12, when viewed sequentially in the left-right direction, the rectangular window function 54b of target data and the rectangular window function 54c of opposing data are alternately present, and there is no position where both are present. This means that there is no pixel in which the back projection process is executed using both target data and opposing data. Accordingly, in the example shown in FIG. 12, spatial resolution can be improved compared to the example of FIG. 13 or 14.

In the example shown in FIG. 13, when viewed sequentially in the left-right direction, in the inclined portions (near the end portion of the X-ray beam) of the isosceles trapezoidal window function 54d of target data and window function 54e of opposing data, both window portions are present, and only one of the window portions is present in the other portion, that is, near the center of the X-ray beam. In a portion where both target data and opposing data are used, since image noise can be reduced, in the example shown in FIG. 13, spatial resolution can be improved near the center of the X-ray beam, and image noise can be reduced near the end portion of the x-ray beam.

In the example shown in FIG. 14, when viewed sequentially in the left-right direction, both the isosceles triangular window function 54f of target data and window function 54g of opposing data are constantly present. In a portion where both target data and opposing data are used, since image noise can be reduced, in the example shown in FIG. 14, image noise can be reduced compared to the example of FIG. 13 or 14.

In the sense of improving spatial resolution, it is desirable to use the window function 54 of the example shown in FIG. 12.

On the other hand, since image noise and spatial resolution have a trade-off relationship, image noise and spatial resolution may be adjusted in accordance with the purpose of diagnosis or the scanning conditions. Accordingly, the X-ray CT apparatus 1 is configured to receive an instruction about whether to improve spatial resolution or to reduce image noise through the input device 34. The reconstruction arithmetic device 36 is configured to appropriately select a triangular shape, a trapezoidal shape, or a rectangular shape as the shape of the window function 54 on the basis of the instruction which is input through the input device 34.

For example, when improvement of spatial resolution is instructed, the reconstruction arithmetic device 36 selects a rectangular shape as the shape of the window function 54. When reduction in image noise is instructed, the reconstruction arithmetic device 36 selects a triangular shape as the shape of the window function 54. When both improvement of spatial resolution and reduction in image noise are instructed, the reconstruction arithmetic device 36 selects a trapezoidal shape as the shape of the window function 54.

Figure 15:
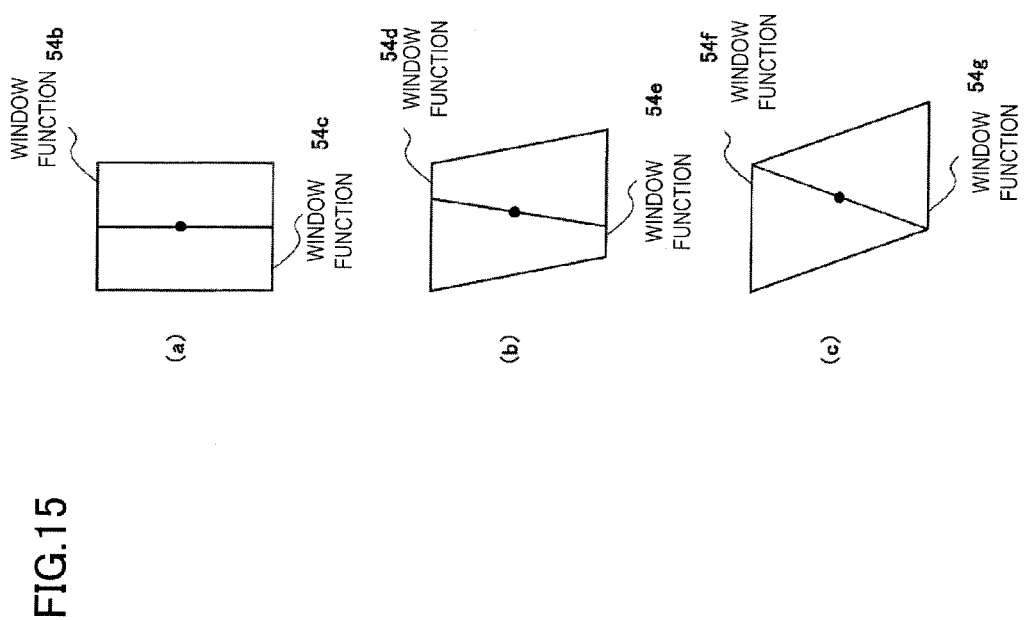
FIG. 15 is an explanatory view of a window function of the invention.
Figure 16:
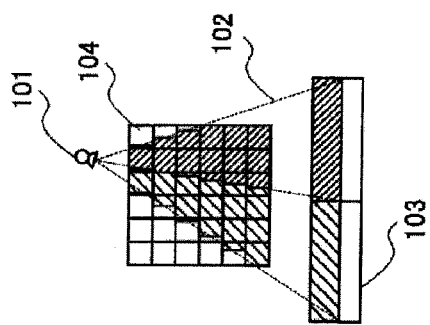
FIG. 16 is an explanatory view of a distance-driven type.

The common property of the examples shown in FIGS. 12 to 14 will be described referring to FIG. 15.

The three examples shown in FIGS. 12 to FIG. 14 have the common property in that the shape of the window function 54 relating to one of target data and opposing data is point symmetrical to the vertically inverted shape of the window function 54 relating to the other one.

FIG. 15(a) shows the window function 54b and the window function 54c of the example shown in FIG. 12. As shown in FIG. 15(a), the shape of the window function 54b is point symmetrical to the vertically inverted shape of the window function 54c (since the window function 54c has a rectangular shape, the shape remains unchanged even if vertically inverted).

FIG. 15(b) shows the window function 54d and the window function 54e of the example shown in FIG. 13. As shown in FIG. 15(b), the shape of the window function 54d is point symmetrical to the vertically inverted shape of the window function 54e.

FIG. 15(c) shows the window function 54f and the window function 54g of the example shown in FIG. 14. As shown in FIG. 15(c), the shape of the window function 54f is point symmetrical to the vertically inverted shape of the window function 54g.

In this way, in more general, the reconstruction arithmetic device 36 executes the back projection process by applying the window function 54 having the above-described common property, making it possible to perform high-resolution reconstruction using opposing data even in the distance-driven back projection process.

It is apparent from the above description that the object of the invention is attained. Although the invention has been described in detail and shown, they are intended for description and illustration, and the invention is not limited to them. It should be noted that the gist of the invention is defined only by the appended claims.

REFERENCE SIGNS LIST

1: X-ray CT apparatus, 2: scanner, 3: operating unit, 4: object, 5: X-ray generation device, 6: collimator, 7: bed, 8: detector, 9: X-ray, 31: input/output device, 32: arithmetic device, 33: display device, 34: input device, 35: storage device, 36: reconstruction arithmetic device, 37: image processing device, 41a, 41b, 41c: back projection phase width, 42a, 42b, 42c: phase in which no opposing data is present, 51: image plane, 52: pixel boundary, 53: beam boundary, 54, 54a, 54b, 54c, 54d, 54e, 54f, 54g: window function, 55: projection value, 56: pixel value

The invention claimed is:

1. An X-ray CT apparatus which performs image reconstruction on the basis of parallel beam data obtained by fan-parallel conversion on fan beam data, the X-ray CT apparatus comprising:
    a determination unit which sets parallel beam data having a phase to be processed as target data, sets parallel beam data having a phase opposing target data as opposing data, and determines the presence/absence of opposing data corresponding to target data; and
    an image reconstruction unit which performs different high-resolution reconstruction depending on the determination result of the determination unit, executes a back projection process on the basis of the distance between a pixel boundary and a beam boundary using target data or target data and opposing data, and performs image reconstruction.

2. The X-ray CT apparatus according to claim 1, further comprising:
    a decision unit which decides a window function representing a rate at which a projection value corresponding to target data or target data and opposing data contributes to a pixel value,
    wherein the image reconstruction unit applies the shape of the window function decided by the decision unit to execute back projection process.

3. The X-ray CT apparatus according to claim 2,
    wherein, when the determination unit determines that opposing data is present, the decision unit decides the window function such that the shape of the window function relating to one of target data and opposing data is point symmetrical to the vertically inverted shape of the window function relating to the other one of target data and opposing data.

4. The X-ray CT apparatus according to claim 3,
    wherein the decision unit sets the shape of the window function relating to target data and opposing data as rectangular shape.

5. The X-ray CT apparatus according to claim 3,
wherein the decision unit is able to select a triangular shape, a rectangular shape, or a trapezoidal shape as the shape of the window function relating to target data and opposing data.

6. The X-ray CT apparatus according to claim 3,
wherein the image reconstruction unit generates an initial image of an iterative process in an iterative approximation method by a filtered back projection method, and executes the iterative process in the iterative approximation method on the basis of the initial image.

7. The X-ray CT apparatus according to claim 1,
wherein the back projection process performs weighting of a pixel value in accordance with the distance between the pixel boundary and the beam boundary.

8. An image reconstruction method which is executed by an X-ray CT apparatus on the basis of parallel beam data obtained by fan-parallel conversion on fan beam data, the image reconstruction method comprising:
  a determination step of setting parallel beam data having a phase to be processed as target data, setting parallel beam data having a phase opposing target data as opposing data, and determining the presence/absence of opposing data corresponding to target data; and
  an image reconstruction step of performing different high-resolution reconstruction depending on the determination result in the determination step, executing aback projection process on the basis of the distance between a pixel boundary and a beam boundary using target data or target data and opposing data, and performing image reconstruction.

\* \* \* \* \*